(12) United States Patent
Barnes

(10) Patent No.: US 8,531,516 B2
(45) Date of Patent: Sep. 10, 2013

(54) IMAGING POLAR NEPHELOMETER

(75) Inventor: John Edward Barnes, Hilo, HI (US)

(73) Assignee: The United States of America as Represented by the Secretary of Commerce, Washington, DC (US)

( * ) Notice: Subject to any disclaimer, the term of this patent is extended or adjusted under 35 U.S.C. 154(b) by 850 days.

(21) Appl. No.: 12/699,272

(22) Filed: Feb. 3, 2010

(65) Prior Publication Data

US 2011/0187850 A1     Aug. 4, 2011

(51) Int. Cl.
*H04N 7/18*          (2006.01)

(52) U.S. Cl.
USPC .......................................... 348/135; 356/339

(58) Field of Classification Search
None
See application file for complete search history.

(56) References Cited

U.S. PATENT DOCUMENTS

| | | | |
|---|---|---|---|
| 4,118,625 A | | 10/1978 | Underwood |
| 4,679,939 A | * | 7/1987 | Curry et al. .................... 356/336 |
| 5,305,073 A | * | 4/1994 | Ford, Jr. ......................... 356/338 |
| 5,541,410 A | * | 7/1996 | Dowben et al. ............... 250/305 |
| 6,731,329 B1 | * | 5/2004 | Feist et al. ..................... 348/135 |
| 6,825,437 B2 | * | 11/2004 | Nakano et al. ........... 219/121.41 |
| 7,126,687 B2 | | 10/2006 | Hill et al. |
| 2009/0039249 A1 | | 2/2009 | Wang et al. |

OTHER PUBLICATIONS

Bigio, Irving, Polar Nephelometer based on azimuthally deflected light, http://onleoglobal.com/services1.html#top, undated.

B. R. Lienert, J. N. Porter, and S. K. Sharma, Aerosol Size Distributions from Genetic Inversion of Polar Nephelometer Data, Hawaii Institute of Geophysics and Planetology, Honolulu, Hawaii, Journal of Atmospheric and Oceanic Technology, vol. 20, Issue 10 (Oct. 2003).
Frank W. Gibson, In situ photometric observations of angular scattering from atmospheric aerosols, Applied Optics, vol. 15, No. 10, Oct. 1976.
John N. Porter et al., Coastal aerosol phase function measurements with a custom polar nephelometer, Ocean Optics XIV Conference, Kona, Hawaii, 1998.
Valery Scherbakov, Light Scattering by Single Natural Ice Crystals, Journal of the Atmospheric Sciences, p. 1513, American Meteorological Society, May 2006.
Jean-Luc Castagner and Irving J. Bigio, Particle sizing with a fast polar nephelometer, Applied Optics, vol. 46, No. 4, Feb. 1, 2007.
Z Ulanowski et al, Laser diffractometer for single-particle scattering measurements, 2002 Meas. Sci. Technol. 13 p. 292-296.
Jean-Luc Castagner and Irving J. Bigio, Polar nephelometer based on a rotational confocal imaging setup, Applied Optics, vol. 45, No. 10, p. 2232-2240, Apr. 2006.
Grams, G. W.; Dascher, A. J.; Wyman, C. M., Laser polar nephelometer for airborne measurements of aerosol optical properties, Optical Engineering, vol. 14, Jan.-Feb. 1975, p. 85-90.

(Continued)

*Primary Examiner* — Christopher S Kelley
*Assistant Examiner* — Christopher Findley
(74) *Attorney, Agent, or Firm* — Robert Platt Bell

(57) ABSTRACT

This invention relates to measuring the light that is scattered from particulates (aerosols) in a gas or liquid. The sample typically flows into the instrument and the particulates are measured in-situ. The intensity of the scattered light is measured at many different angles, which determines both the amount of particulates in the sample, and detailed information about the particles such as average size, shape and composition. The measurement can be applied to climate and air pollution research, and clean room monitoring.

10 Claims, 4 Drawing Sheets

(56) References Cited

OTHER PUBLICATIONS

J-F Gayet, et. al., Microphysical and optical properties of Arctic mixed-phase clouds—the Apr. 9, 2007 case study, Atmos. Chem. Phys. Discuss., 9, 11333-11366, 2009.

Keng H. Leong a; Matthew R. Jones a; Donna J. Holdridge a; Mark Ivey, Design and Test of a Polar Nephelometer, Aerosol Science and Technology, vol. 23, Issue 3 1995, pp. 341-356, Jan. 1, 1995.

Barkey, Brian; Bailey, Matt; Liou, Kuo-Nan; Hallett, John, Light-scattering properties of plate and column ice crystals generated in a laboratory cold chamber, Applied Optics, vol. 41, iss. No. 27, p. 5792-5796, Sep. 2002.

Hideki Kinjo, Hiroaki Kuze, Yasushi Sakurada and Nobuo Takeuchi, Calibration of the Lidar Measurement of Tropospheric Aerosol Extinction Coefficients, Jpn. J. Appl. Phys. 38 (1999) pp. 293-297, Sep. 1998.

Hansen, M. Z.; Evans, W. H., Polar nephelometer for atmospheric particulate studies, Applied Optics, vol. 19, Oct. 1, 1980, p. 3389-3395. Oct. 1980.

D.S. McCall et al. Investigation into Single Scattering Properties of Airborne Saharan Dust Particles Eleventh Conf. on Electromagnetic & Light Scattering, pp. 129-133. undated.

O. Crepel, J.-F. Gayet1, J.-F. Fournol and S. Oshchepkov, A new airborne Polar Nephelometer for the measurement of optical and microphysical cloud properties. Part II: Preliminary tests, Annales Geophysicae, vol. 15, No. 4 / Apr. 1997, p. 46-470.

Barnes, J. E.; Bronner, S.; Beck, R.; Parikh, N. C.;. Boundary layer scattering measurements with a CCD camera lidar, Applied Optics, 42, 2647-2652, 2003.

Barnes, John E., N. C. Parikh Sharma and Trevor B. Kaplan, Atmospheric aerosol profiling with a bistatic imaging lidar system, Applied Optics, 46, 2922-2929, May 2007.

Kaller, W., A new polar nephelometer for measurement of atmospheric aerosols, J. of Quantitative Spectroscopy & Radiative Transfer, 87, 107-117 (2004).

Barkey, B. and K. N. Liou, Polar nephelometer for light-scattering measurements of ice crystals, Optics Letter, 26, 232-234 (2001).

Gayet, J. F., O. Crepel, J. F. Fournol and S. Oshchepkov, A new airborne polar Nephelometer for the measurements of optical and microphysical cloud properties. Part I: Theoretical design, Ann. Geophysicae, 15, 451-459 (1997).

* cited by examiner

– 1 –

IMAGING POLAR NEPHELOMETER

STATEMENT OF GOVERNMENT INTEREST

The research that led to the development of the present invention was sponsored by the National Oceanic and Atmospheric Administration's (NOAA's) Global Monitoring Division. NOAA is a part of the U.S. Department of Commerce, a component of the U.S. Federal government. The United States Government has certain rights in the present invention.

FIELD OF THE INVENTION

The present invention relates to a nephelometer. In particular, the present invention is directed toward an imaging polar nephelometer, which uses imaging techniques and a single CCD camera to characterize particle size and type using pixel counting techniques.

BACKGROUND OF THE INVENTION

An instrument known as an integrating nephelometer has been in existence for many years for measuring the amount of light scattered by particulates (aerosols) in the air. Several commercial integrating nephelometers are available from companies such as TSI Inc. (Minnesota), Radiance Research (Washington), and Optec Inc. (Michigan). The instruments are sold for monitoring air pollution, for atmospheric and climate research, and for monitoring clean rooms. These instruments are called integrating nephelometers because they measure the total light scattered at all angles altogether. Much information is lost about the particulates because their size, shape and composition influence the angles at which the light is scattered.

A polar nephelometer (as in a mathematical polar plot using angle and radius) is able to measure the light scattered at individual angles. As will be discussed in more detail below, there have been several research instruments built by different research groups, using multiple detectors or moveable arm-mounted detectors. There are no known commercial instruments developed from such research devices, as they are relatively complex and expensive to build, and also difficult to use for field implementations. Thus it remains a requirement in the art to provide a simpler design, higher sensitivity, and higher resolution that these Prior Art research devices, and provide them in an apparatus that can be readily commercialized.

The following two publications detail the technique of creating and analyzing a wide-angle camera image of a laser beam to measure particulates: Barnes, J. E.; Bronner, S.; Beck, R.; Parikh, N. C.; *Boundary layer scattering measurements with a CCD camera lidar*, Applied Optics, 42, 2647-2652, 2003, and Barnes, John E., N. C. Parikh Sharma and Trevor B. Kaplan, *Atmospheric aerosol profiling with a bistatic imaging lidar system*, Applied Optics, 46, 2922-2929, May, 2007, both of which are incorporated herein by reference.

There are many publications of research polar nephelometers using multiple detectors, single detectors on movable arms or variations of these. The following are three examples: Kaller, W., *A new polar nephelometer for measurement of atmospheric aerosols*, J. of Quantitative Spectroscopy & Radiative Transfer, 87, 107-117 (2004), Barkey, B. and K. N. Liou, *Polar nephelometer for light-scattering measurements of ice crystals*, Optics Letter, 26, 232-234 (2001), Gayet, J. F., O. Crepel, J. F. Fournol and S. Oshchephov, *A new airborne polar Nephelometer for the measurements of optical and microphysical cloud properties. Part I: Theoretical design*, Ann. Geophysicae, 15, 451-459 (1997), all of which are incorporated herein by reference.

Hill et al., U.S. Pat. No. 7,126,687, issued Oct. 24, 2006 and incorporated herein by reference, discloses a method and apparatus for determining absorption and morphology of individual airborne particles. In particular, the Hill device uses a single probe laser and a number of trigger lasers in combination with a plurality of detectors to measure two-dimensional optical scattering at different wavelengths.

Wang et al., Published U.S. Patent Application No. 2009/0039249, published Feb. 12, 2009, and incorporated herein by reference, discloses a size segregated aerosol mass concentration measurement device. Wang uses an integrating signal conditioner to integrate the electronic signal from his detector.

In general, the polar nephelometers of the Prior Art have complicated designs which are also are not very sensitive. They use multiple detectors or rotating mirrors to get the angular information instead of creating an image. Some are able to measure individual particles, which can be an advantage for some scientific work. But such instruments may not be suitable for the commercial integrating nephelometer market. A need still exists in the art for a simplified imaging polar nephelometer, which can measure average light scattered from all the air and particles in a chamber.

SUMMARY OF THE INVENTION

The present invention relates to measuring light scattered from particulates (aerosols) in a gas or liquid. The sample typically flows into the instrument and the particulates are measured in-situ. The intensity of the scattered light is measured at many different angles, which determines both the amount of particulates in the sample, and detailed information about the particles such as average size, shape and composition. The measurement can be applied to climate and air pollution research, and clean room monitoring.

The polar nephelometer of the present invention uses a laser as a light source. The laser is directed through a window into an enclosed sample chamber, where the beam traverses the length of the chamber and exits at the opposite end. A scientific-grade CCD camera and very wide-angle lens (greater than 170 degrees) are positioned in the center of the sample chamber and image the light scattered by molecules and aerosols in the path of the beam. The sample air continuously flows through the chamber.

The plane of polarization of the incident beam can be varied between vertical, horizontal or circular to get more information about the particles. The circular polarization is equivalent to unpolarized light in this application. The sample air can be diverted through a filter to remove the particles for calibration measurements of pure molecular scattering.

Several beams with different polarizations and wavelengths may be measured simultaneously by the single camera lens, providing additional information about the particles. The shortest time for a useful measurement is on the order of a few seconds. Longer averaging times are easily accomplished by lengthening the camera exposure time.

There are a number of features and advantages of the present invention. Three prominent features of the present invention include: 1) Wide-angle optics (lenses and/or mirrors) create an image of a laser beam including a wide range of scattering angles (nearly 0 to 180 degrees) with high resolution; 2) The image can be recorded by a digital CCD camera or other type of image detector (like CMOS or photodiode arrays); 3) Pure molecular scattering can be used to calibrate the angles, total light, and polarization of the polar nephelometer.

With regard to the first point, the inventor has used a panoramic mirror and a cylindrical mirror to get a wide-angle image of the entire laser beam. However, others, such as Hill et al., U.S. Pat. No. 7,126,687, are actually using a concave (ellipsoidal) mirror to get a wide-angle image at a single point where the laser and the air/aerosol flow intersects the laser. This is fundamental difference from the present invention. Several others have used this kind of configuration, such as Wang et al., Published U.S. Patent Application No. 2009/0039249, by getting various angles from a single intersection point. One even uses a CCD. But none of these Prior Art devices images the whole laser beam as in the present invention. Imaging the entire beam allows the present invention to be much more sensitive than the Prior Art devices.

With regard to the third point, other Prior Art instruments could theoretically use pure molecular scattering to calibrate the angles, total light, and polarization of the polar nephelometer, if they were sensitive enough. However, the present invention, as noted below, has the sensitivity to accomplish this and represents the first practical application of this technique known to the inventor.

The polar nephelometer of the present invention may be produced at equal or lower cost than Prior Art devices, and yet provide much more detailed information about the particles. Data taken from this invention can already characterize the particle size distribution. The data can potentially characterize particle shape and light absorption properties as well.

The present invention has high angular resolution, has a simple design, and is sensitive enough to measure the molecular scatter. The absolute calibration has been shown to be a few percent or better.

DETAILED DESCRIPTION OF THE INVENTION

Figure 1:
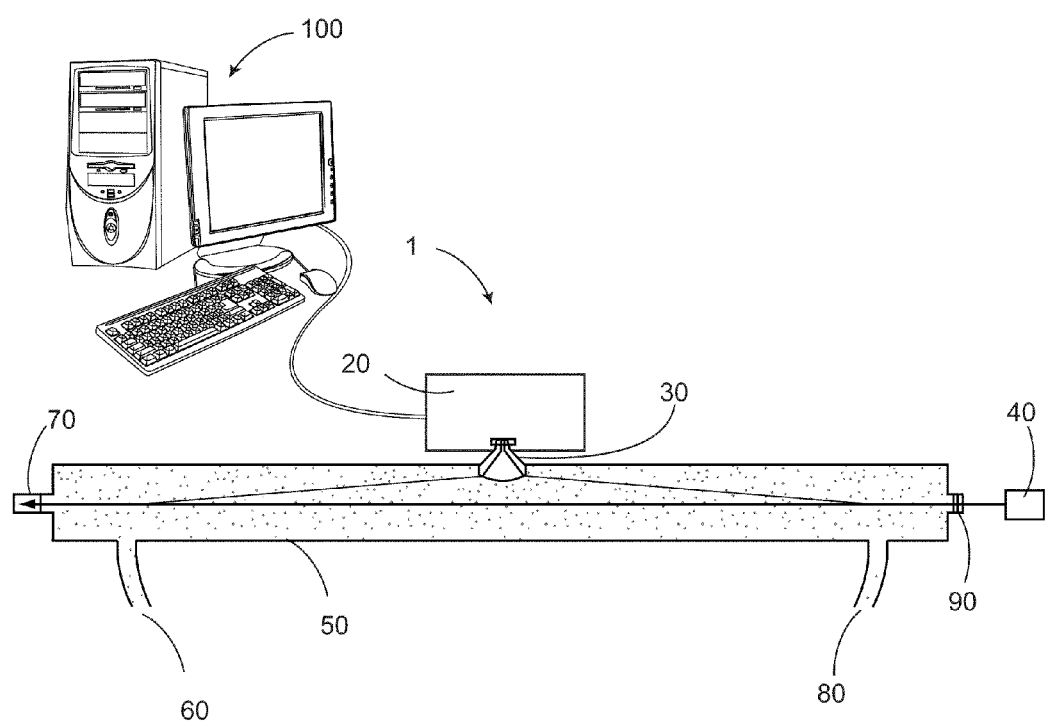
FIG. 1 is a diagram of the imaging polar nephelometer of the present invention, where light is scattered from the laser beam by both molecules and particulates and an image of the beam is recorded by the wide-angle lens and camera.

FIG. 1 is a diagram of the imaging polar nephelometer of the present invention, where light is scattered from the laser beam by both molecules and particulates and an image of the beam is recorded by the wide-angle lens and camera. The instrument 1 uses a laser 40 as a light source. Laser 40 is directed through a window 90 into an enclosed sample chamber 50, where the beam traverses the length of chamber 50 and exits at the opposite end 70. A scientific-grade CCD camera 20 and very wide-angle lens 30 (greater than 170 degrees) are positioned in the center of the sample chamber and image the light scattered by molecules and aerosols in the path of the beam. The sample air continuously flows through the chamber from inlet port 80 to outlet port 60. Data from camera 20 may be transmitted to computer 100, which may comprise a typical PC-type computer known in the art. Software described below and attached in the Appendix submitted herewith, may be used to process the image data.

The plane of polarization of the incident beam can be varied between vertical, horizontal or circular to get more information about the particles. The circular polarization is equivalent to unpolarized light in this application. The sample air can be diverted through a filter to remove the particles for calibration measurements of pure molecular scattering. This is an important step to get absolutely calibrated measurements.

Only one light beam is shown in FIG. 1, but several beams with different polarizations and wavelengths may be measured simultaneously by the single camera 20 and lens 30 to provide additional information about the particles. The shortest time for a useful measurement is on the order of a few seconds. Longer averaging times are easily accomplished by lengthening the camera exposure time.

Figure 2:
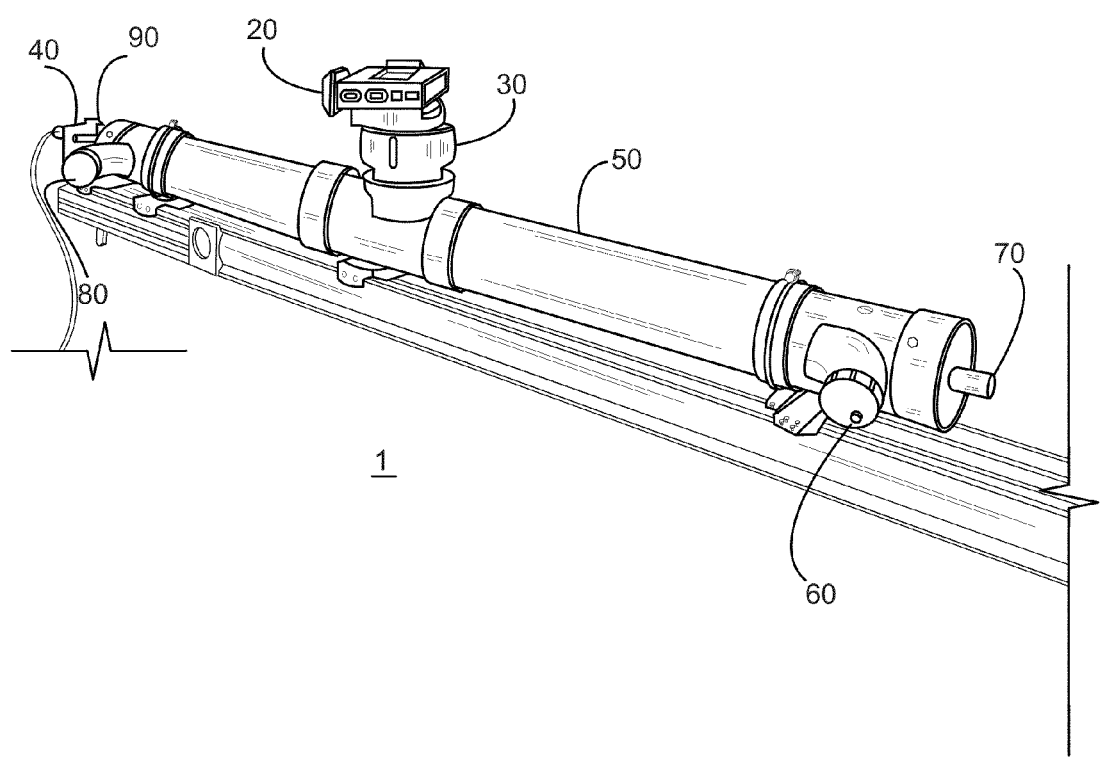
FIG. 2 is an illustration of the first working version of the invention, where the polar nephelometer is shown with the laser to the left of the sample tube, and the camera and wide-angle lens located on top.

The first working version of the invention is shown in FIG. 2. As illustrated in Figure, the polar nephelometer 1 is shown with the laser 40 to the left of the sample tube 50, and the camera 20 and wide-angle lens 30 located on top. Camera 20 may comprise a Santa Barbara Instrument Group (SBIG), Model ST-8 camera, manufactured by Santa Barbara Instrument Group of Santa Barbara, Calif. Lens 30 may comprise a Coastal Optical Systems, 185 Fisheye Digital SLR lens, manufactured by Coastal Optical Systems of West Palm Beach, Fla. Laser 40 may comprise a Dragon Laser Model PGL-FS, 50 mW, continuous, 532 nanometer wavelength laser made by Dragon Laser ChangChun Dragon Lasers Co., Ltd, Nan Guan, ChangChun, JiLin, China.

The Polarizing optics may comprise a CVI, quarter wave plate. The Analyzing software was written in-house using the Interactive Data Language (IDL). Other hardware may be used within the spirit and scope of the present invention. For example, the apparatus may be modified to use a smaller chamber, smaller camera, and smaller lens. The panoramic mirror tested earlier used an H3G panoramic mirror from Neovision S. R. O. of the Czech Republic.

As illustrated in FIG. 2, sample tube 50 may be made from PCV tubing, as in this prototype. However, other types of tubing, such as aluminum, glass, or the like may be used within the spirit and scope of the present invention. To provide an imaging background, sample tube 50 may be lined with a fabric (e.g., black velvet cloth or the like) or may be suitably coated with a non-reflective light-absorbing material to provide a good background for the image received by camera 20.

The simple camera/lens in the present invention takes advantage of the well-designed lenses available from commercial companies. Other optical schemes such as a panoramic mirror or cylindrical mirror, may also be used to create an image. The wide-angle lens, however, is the preferred embodiment in the present invention. There are several other geometries, which may be used within the spirit and scope of the present invention, such as putting the camera at one end of the tube and reflecting the laser beam back through the tube for separate forward and backward beam images. Such an embodiment may make the whole instrument shorter.

Figure 3:
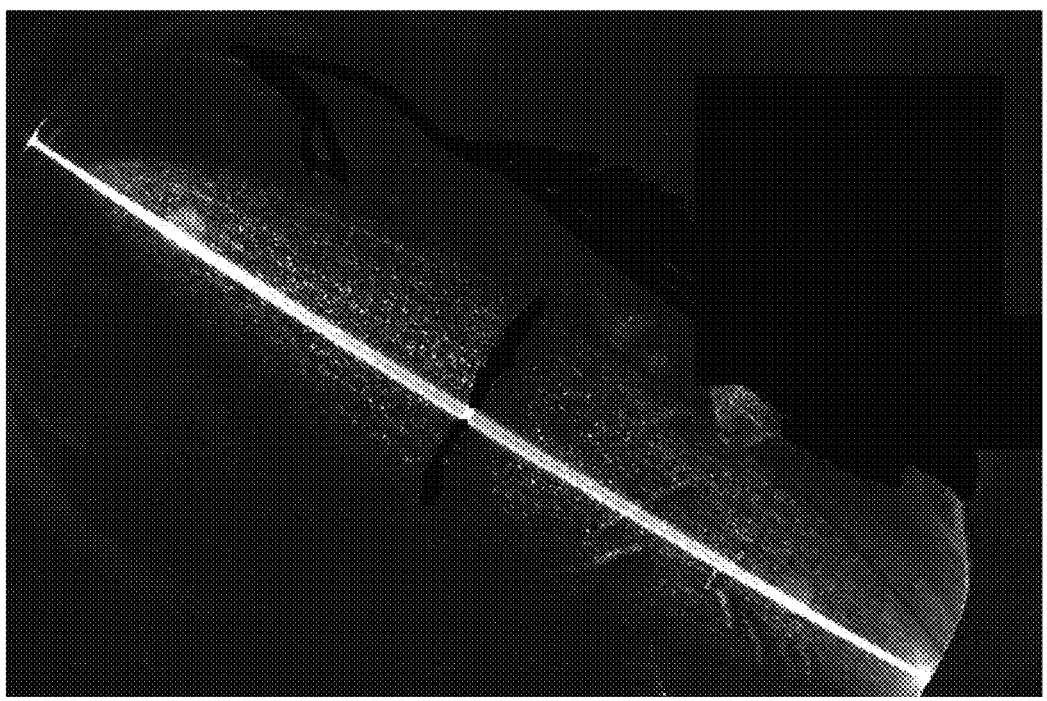
FIG. 3 illustrates an example of a typical image recorded by the camera.

FIG. 3 is an actual image recorded by camera 20 in the prototype device of FIG. 2. The laser enters from the top left of the image (5 degrees) and exits at the bottom right (175 degrees). The chamber is covered with an optically dark fabric to improve the image analysis. Various artifacts can be seen where the laser light is scattered by folds and joints in the fabric in this prototype. However, in a production model, these folds are eliminated, reducing or eliminating the amount of artifacts. The beam is analyzed by starting at one end of the beam and adding up the pixel counts at each point along the beam. Each point along the beam corresponds to a different angle. The pixel resolution of this polar nephelometer is about 0.11 degrees per pixel.

Figure 4:
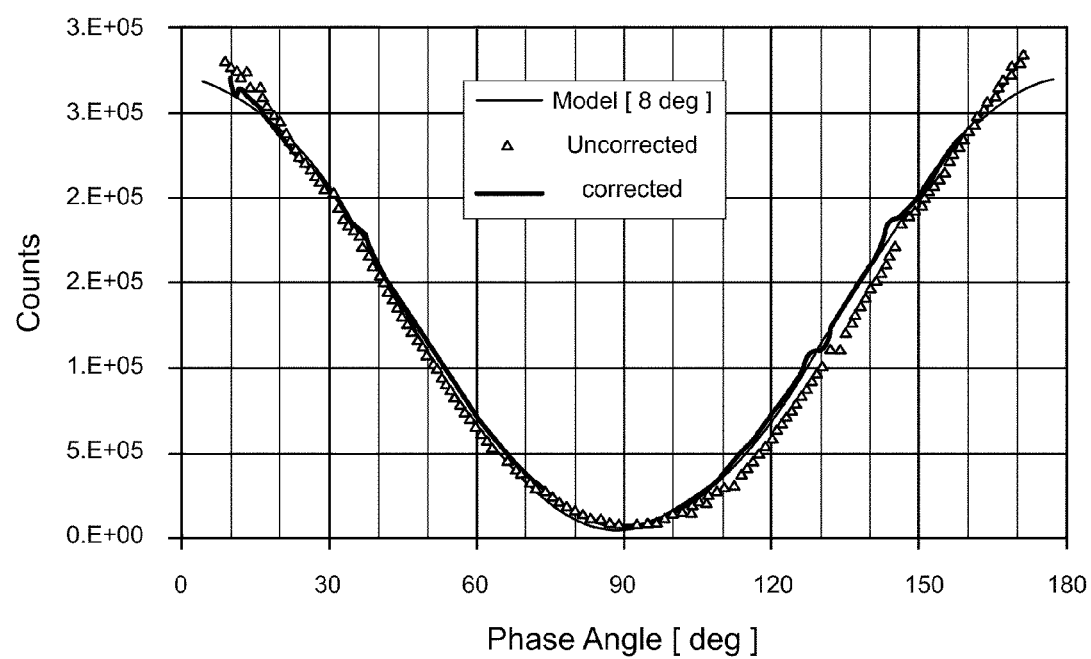
FIG. 4 is a graph illustrating the molecular phase function calibration.

An image of filtered air (no particulates), such as shown in FIG. 3, may be periodically be taken for calibration of the polar nephelometer. The molecular contribution can then be subtracted from the total signal measured during operation leaving the particulate scattered light. This procedure is very similar to the way an integrating nephelometer is calibrated. For the polar nephelometer the molecular scatter intensity, I, follows:

$$I \propto (\sin^2(\phi) + \cos^2(\theta) * \cos^2(\phi)),$$

where $\phi$ is the laser polarization and $\theta$ is the phase function angle. It is extremely important to be able to accurately measure the molecular phase function. It provides an absolute calibration of the total intensity, of the relative changes with angle, and of the angle calibration. An example of the power of this calibration is shown in FIG. 4. The laser was not completely parallel polarized ($\phi=0$ deg) and the best fit is $\phi=8$ deg. The molecular model is shown with the analyzed data averaged to one-degree resolution. The uncorrected data clearly show the angle must be offset slightly; in this case one degree. The precision of this adjustment, in fact, is much better than one degree.

There are also two simple corrections that can directly be applied. One adjusts the angles slightly (roughly one degree or less) to account for the change in the image distance in the focusing optics. The other is a geometric factor that adjusts the signal at extreme angles for the finite size of the pixels. The corrected line in FIG. 4 has had both of these adjustments made. There is some deviation at very small and very large angles due to scattered light in the instrument. This can be corrected by various techniques including installing optical baffles.

The invention's sensitivity is illustrated in FIG. 4. For monitoring particulates, a user may want to have an absolute calibration on how much light the particles are scattering. With the present invention, one can measure pure air, which has very well-known properties and helps to tell if the instrument is working properly. None of the other polar nephelometers of the Prior Art are known to calibrate pure air. For example, the device disclosed in *Polar nephelometer based on a rotation confocal imaging setup*, (Jean Luc Castagner and Irving J. Bligo, Applied Optics, vol. 45, No. 10, Apr. 1, 2006, incorporated herein by reference) uses small synthetic spheres suspended in water for calibration, but this isn't nearly as convenient as just switching the inlet air through a filter to take out the particulates, which is the way the present invention is calibrated. While some commercial integrating nephelometers have an automatic pure air calibration, no polar nephelometers of the Prior Art are known to calibrate pure air. The present invention can run a calibration every hour, if need be. Sometimes other gases (like carbon dioxide) may be used for the pure molecular scatter calibration.

As noted with regard to FIG. 1, computer 100 may be used to process the image data, using a pixel counting technique of the present invention. The pixel counting technique may be performed in two ways. For images where the beam lies along a few rows of pixels, the value of each pixel that lies on a perpendicular line at the point being analyzed can be added together. This total represents the total light scattered at this point along the beam. The average background noise can be estimated by averaging pixels that lie on the perpendicular further away from the beam. In the case where the beam cuts across rows on a diagonal, a very general method has been used. The same perpendicular line to the beam is calculated, and values along the perpendicular are determined from a two-dimensional interpolation routine (since the perpendicular doesn't necessarily go through the pixel centers). The points along the perpendicular define a beam cross-section. A curve-fit of a peak shape (for example a bell shaped curve) is made to the beam cross-section, which gives the background noise, beam width, and the total light at that point along the beam.

Software for the pixel counting technique was written in-house at the direction of the inventor, and runs on a standard PC 100. The programming language is the Interactive Data Language (IDL) from ITT Visual Information Solutions. The Attached Appendix contains source code for the software used in the present invention to count pixels from the CCD camera and convert this data into particle data. The implemented source code was written by Trevor Kaplan, under the supervision of the present inventor. The algorithms used in the source code were developed by the present inventor.

In the prototype described in FIG. 2, a standard interference filter may be used to select just the laser wavelength and block other light. The filter (not shown) may be located between lens 30 and camera 30. In the preferred embodiment, such a filter may not be required, as is already quite dark inside the instrument and without a filter it is easy to use a second wavelength. The filters usually block all other wavelengths although some custom designed ones may be able to transmit two wavelengths. Such filters are commonly used in instruments to reduce background light. They can introduce some measurement problems, however, the pure air (molecular scatter) calibration of the present invention compensates for such errors.

While the preferred embodiment and various alternative embodiments of the invention have been disclosed and described in detail herein, it may be apparent to those skilled in the art that various changes in form and detail may be made therein without departing from the spirit and scope thereof.

I claim:

1. An imaging polar nephelometer for measuring particle information in a fluid, comprising:
    a sample tube having a first end accepting a fluid sample and a second end exhausting the fluid sample;
    a laser, mounted to one end of the sample tube and directing a light beam down a length of the sample tube, illuminating particles in the fluid sample;
    a CCD camera, mounted to the sample tube, imaging particles illuminated within the sample tube and outputting a digital image of illuminated particles in the sample tube;
    one of a wide angle lens, coupled between the CCD camera and the sample tube, a panoramic mirror, mounted in the sample tube, and a cylindrical mirror, mounted in the sample tube, expanding the scope of imaging of the CCD camera to encompass a substantial portion of the sample tube; and
    a digital image processor, coupled to the CCD camera, receiving the digital image of scattered light from illuminated particles in the sample tube, processing the digital image to sum values of each pixel that lies on a perpendicular line at the point along the light beam to produce a total representing total light scattered at that point along the beam, and outputting the sums of the values of the pixels at a plurality of points along the light beam in the digital image as an indication of particle information within the fluid sample,
    wherein the digital image processor measures molecular scatter intensity, I, as:

$$I \propto (\sin^2(\phi) + \cos^2(\theta) * \cos^2(\phi)),$$

where φ is the laser polarization and θ is the phase function angle.

2. The imaging polar nephelometer of claim 1, further comprising:
an inlet filter, coupled to the first end of the sample tube selectively filtering the fluid sample to remove particles for calibration of the imaging polar nephelometer.

3. The imaging polar nephelometer of claim 1, wherein the digital image processor outputs an indication of one or more of particle size, shape, and composition within the fluid sample based on the sum of values of each pixel that lies on a perpendicular line at the point along the light beam.

4. The imaging polar nephelometer of claim 1, further comprising:
an image corrector, correcting the digital image of illuminated particles in the sample tube, the image corrector adjusting image angles by small predetermined amounts to account for the change in the image distance in focusing optics of the CCD camera.

5. The imaging polar nephelometer of claim 1, further comprising:
an image corrector, correcting the digital image of illuminated particles in the sample tube, the image corrector comprising a geometric factor adjusting the image of illuminate particles at extreme angles for the finite size of the pixels.

6. A method of measuring particle content in a fluid, comprising:
passing a fluid sample through a sample tube having a first end accepting the fluid sample and a second end exhausting the fluid sample,
illuminating particles in the fluid sample with a laser, mounted to one end of the sample tube and directing a light beam down a length of the sample tube,
outputting a digital image of illuminated particles in the sample tube using a CCD camera, mounted to the sample tube, imaging particles illuminated within the sample tube,
expanding the scope of the digital imaging of the CCD camera to encompass a substantial portion of the sample tube using one of a wide angle lens, coupled between the CCD camera and the sample tube, a panoramic mirror, mounted in the sample tube, and a cylindrical mirror, mounted in the sample tube, and
processing the digital image to sum values of each pixel that lies on a perpendicular line at a point along the light beam to produce a total representing total light scattered at that point along the beam, in a digital image processor, coupled to the CCD camera and receiving the digital image of illuminated particles in the sample tube,
outputting the sums of the values of the pixels at a plurality of points along the light beam in the digital image as an indication of particle information within the fluid sample, and
measuring molecular scatter intensity, I, in the digital image processor as:

$$I \propto (\sin^2(\phi) + \cos^2(\theta) * \cos^2(\phi)),$$

where φ is the laser polarization and θ is the phase function angle.

7. The method of measuring particle content in a fluid of claim 6, further comprising filtering the fluid sample to remove particles for calibration using an inlet filter, coupled to the first end of the sample tube.

8. The method of measuring particle content in a fluid claim 6, wherein the digital image processor outputs an indication of one or more of particle size, shape, and composition within the fluid sample based on sum values of each pixel that lies on a perpendicular line at the point along the light beam.

9. The method of measuring particle content in a fluid of claim 6, further comprising:
correcting the digital image of illuminated particles in the sample tube using an image corrector adjusting image angles by small predetermined amounts to account for the change in the image distance in focusing optics of the CCD camera.

10. The method of measuring particle content in a fluid of claim 6, further comprising:
correcting the digital image of illuminated particles in the sample tube using an image corrector comprising a geometric factor adjusting the digital image of illuminated particles at extreme angles for the finite size of the pixels.

* * * * *